(12) United States Patent  (10) Patent No.: US 8,994,815 B2
Mito et al.  (45) Date of Patent: Mar. 31, 2015

(54) METHOD OF EXTRACTING CONTOUR LINES OF IMAGE DATA OBTAINED BY MEANS OF CHARGED PARTICLE BEAM DEVICE, AND CONTOUR LINE EXTRACTION DEVICE

(75) Inventors: Hiroaki Mito, Hitachinaka (JP); Ryoichi Matsuoka, Yotsukaido (JP)

(73) Assignee: Hitachi High—Technologies Corporation, Tokyo (JP)

( * ) Notice: Subject to any disclaimer, the term of this patent is extended or adjusted under 35 U.S.C. 154(b) by 353 days.

(21) Appl. No.: 13/523,000

(22) PCT Filed: Jan. 20, 2011

(86) PCT No.: PCT/JP2011/050965
§ 371 (c)(1),
(2), (4) Date: Jul. 19, 2012

(87) PCT Pub. No.: WO2011/090111
PCT Pub. Date: Jul. 28, 2011

(65) Prior Publication Data
US 2012/0300054 A1 Nov. 29, 2012

(30) Foreign Application Priority Data
Jan. 22, 2010 (JP) ................................ 2010-011562

(51) Int. Cl.
*H04N 7/18* (2006.01)
*H01J 37/28* (2006.01)
(Continued)

(52) U.S. Cl.
CPC ............ *H01J 37/28* (2013.01); *G01N 23/2251* (2013.01); *G06T 7/0083* (2013.01);
(Continued)

(58) Field of Classification Search
USPC ............. 348/79, 125–127, 130, 133, 134, 80; 382/144–150; 250/306–311
See application file for complete search history.

(56) References Cited

U.S. PATENT DOCUMENTS 4,878,177 A * 10/1989 Ikenaga et al. ................... 716/52
6,148,118 A 11/2000 Murakami et al.
(Continued)

FOREIGN PATENT DOCUMENTS

JP 60-169977 A 9/1985
JP 6-325176 A 11/1994
(Continued)

OTHER PUBLICATIONS

International Search Report including English language translation dated Feb. 22, 2011 (Four (4) pages).

*Primary Examiner* — Michael Lee
(74) *Attorney, Agent, or Firm* — Crowell & Moring LLP

(57) ABSTRACT

The present invention is intended to provide a contour extraction method and a contour extraction device with an objective of either suppression of unnecessary contouring processings or selective contouring of necessary portions. To attain the objective, provided are a contour extraction method, and a device, with which contours of pattern edges on an image formed based on charged particles emitted from a sample are extracted and, when contouring of a pattern located in an overlapping region provided in connecting images of plural image-capturing regions to form a synthesized image is performed, either areas of the pattern in the plurality of image-capturing regions, or a pre-set measurement portion is found, and selective contour extraction of the pattern with respect to an image of an image-capturing region is carried out either on a side where the area is large, or on a side where a measurement portion regarding the pattern is located.

9 Claims, 19 Drawing Sheets

(51) Int. Cl.
*G01N 23/225* (2006.01)
*G06T 7/00* (2006.01)
*H01J 37/22* (2006.01)
*G01B 15/04* (2006.01)
*H01L 21/66* (2006.01)

(52) U.S. Cl.
CPC .............. *H01J 37/222* (2013.01); *G01B 15/04* (2013.01); *G06T 2207/10061* (2013.01); *G06T 2207/30148* (2013.01); *H01J 2237/221* (2013.01); *H01J 2237/24592* (2013.01); *H01J 2237/2817* (2013.01); *H01L 22/12* (2013.01); *G01B 2210/56* (2013.01)
USPC ............ 348/133; 348/126; 348/80; 382/145; 382/149

(56) References Cited

U.S. PATENT DOCUMENTS

| | | | |
|---|---|---|---|
| 6,396,960 | B1 | 5/2002 | Yoshimura |
| 6,647,147 | B1 * | 11/2003 | Miyano ..................... 382/199 |
| 7,454,051 | B2 * | 11/2008 | Hirano et al. ................. 382/144 |
| 7,983,471 | B2 * | 7/2011 | Kitamura et al. ............. 382/145 |
| 2004/0181361 | A1 * | 9/2004 | Ikeda et al. ................... 702/159 |
| 2008/0210862 | A1 * | 9/2008 | Yamaguchi et al. .......... 250/291 |
| 2009/0039261 | A1 | 2/2009 | Toyoda et al. |
| 2009/0039263 | A1 | 2/2009 | Matsuoka et al. |
| 2009/0202137 | A1 | 8/2009 | Shinoda et al. |

FOREIGN PATENT DOCUMENTS

| | | |
|---|---|---|
| JP | 8-161508 A | 6/1996 |
| JP | 9-23330 A | 1/1997 |
| JP | 9-204529 A | 8/1997 |
| JP | 11-17924 A | 1/1999 |
| JP | 2004-72533 A | 3/2004 |
| JP | 2005-79274 A | 3/2005 |
| JP | 2008-252716 A | 10/2008 |
| JP | 2009-43937 A | 2/2009 |
| JP | 2009-44070 A | 2/2009 |
| JP | 2009-157543 A | 7/2009 |

* cited by examiner

METHOD OF EXTRACTING CONTOUR LINES OF IMAGE DATA OBTAINED BY MEANS OF CHARGED PARTICLE BEAM DEVICE, AND CONTOUR LINE EXTRACTION DEVICE

TECHNICAL FIELD

The present invention is concerned with a method of extracting contour lines of an image data and a contour line extraction device, and pertains in particular to a method of extracting contour lines of an image data and a contour line extraction device capable of improvement in the efficiency of contouring processings.

BACKGROUND ART

Along with the miniaturization of semiconductor devices, there has been an increase in unpredictable defects for which it is impossible to specify the positions in advance so that it has become a problem that the time that it takes to launch production due to the inspection of the defects is increasing. As a result, in order to aim for improvement in the efficiency of defect detection, there is a need to implement pattern defect detection on the full face, or a size close thereto, of a single shot within a wafer.

As a technique therefor, there is known a charged particle beam device that acquires a plurality of images of small regions (with widths of several microns) and forms one synthesized image by joining these together (may be referred to as panoramization, hereinafter) to perform defect detection or measurement.

In Patent Literature 1, a technique is disclosed to carry out panorama synthesis of semiconductor circuit patterns while easiness of matching is enhanced by analyzing design data of patterns in a stage prior to capturing images of patterns and carrying out image capturing of the patterns so that patterns for which it is easy to specify synthesized positions of images fall in the overlapping regions between the images subject to synthesis.

Besides, techniques of evaluating the quality of a pattern by measuring not only the width of the pattern but also the two-dimensional profile of the pattern have gradually been adopted. Since pattern edges displayed in images obtained with an electron microscope or the like have a certain width due to the edge effect and the profile thereof is difficult to specify, pattern edge contouring technology is known as a technique for carrying out accurate two-dimensional measurements. Contouring is technology that, on the basis of the brightness distribution of the pattern edges, narrows the edge portions into thin lines. In Patent Literature 2, there is described technology that panoramizes pattern information converted into narrow lines.

CITATION LIST

Patent Literature

Patent Literature 1: JP-A-2009-157543 (corresponding to U.S. Patent Application Publication US2009/0202137)
Patent Literature 2: JP-A-2009-043937 (corresponding to U.S. Patent Application Publication US2009/0039263)

SUMMARY OF INVENTION

Technical Problem

As for panoramization technology such as described in Patent Literature 1, it is possible to measure regions of wide ranges subject to measurements with images of high resolution and, further, as described in Patent Literature 2, panoramization of thinned (contoured) images enables two-dimensional measurement over a wide range with high precision. On the other hand, in order to form a panorama image, it is needed to overlap parts of the fields of view of an electron microscope or the like and to form a synthesized image so as to match the overlaid regions; when contouring processing is carried out separately in each of the image-capturing regions, it turns out that contouring processing is carried out a plurality of times regarding the overlaid regions. In particular, in a region where four images are overlapped, contouring processing is carried out four times regardless of the fact that they are patterns of the same profile, which is inefficient.

Hereinafter, there is given a description regarding a contour line extraction method and a contour line extraction device with an objective of either suppression of unnecessary contouring processings or selective contouring of necessary portions.

Solution to Problem

As a mode for attaining the aforementioned objective, in a contour line extraction method, and a device, with which contour lines of pattern edges on an image formed based on charged particles emitted from a sample are extracted, provided are a method and a device for contour line extraction, with which, when contouring of a pattern located in an overlaid region provided in connecting images of a plurality of image-capturing regions to form a synthesized image is performed, either areas of the pattern in the aforementioned plurality of image-capturing regions, or a portion of measurement set in advance is found, and selective contour line extraction of the aforementioned pattern with respect to an image of an image-capturing region either on a side where the area is large, or on a side where a portion of measurement regarding the pattern is located is carried out.

Also, as other modes, there are proposed a contour line extraction method and a device, in which selective extraction of contour lines are executed for given measurement regions surrounding a part of measurement, a part of pattern, and/or a pattern set in advance.

Advantageous Effects of Invention

According to the aforementioned configurations, it becomes possible to implement greater efficiency in measurements and inspections using contour line information since redundant processing of contouring or contouring processing of unnecessary portions can be suppressed.

Other objects, features, and advantages of the invention will become apparent from the following description of the embodiments of the invention taken in conjunction with the accompanying drawings.

DESCRIPTION OF EMBODIMENTS

Hereinafter, using the drawings descriptions in detail regarding a technique of forming contour lines of a pattern, a device forming contour lines of a pattern, and a computer program executed in the device on the basis of a charged particle beam image are given.

More specifically, there is given a description regarding a technique of extracting pattern contour lines based on image data acquired with a Critical Dimension Scanning Electron Microscope (CD-SEM), which is a kind of measurement devices. Incidentally, in the undermentioned description, a CD-SEM, which is a device to measure pattern dimensions, is described as an example of an image acquisition device, but application to a device to inspect pattern defects is also possible. Further, in the undermentioned description, there is described an example using an SEM as a mode of a charged particle beam device, but it is not limited hereto; it is also acceptable, for example, that a Focused Ion Beam (FIB) device, which scans an ion beam on a sample to form an image, is adopted as the charged particle beam device. However, since an exceedingly high magnification is required in order to measure patterns for which miniaturization is advancing with great precision, it is preferable to use an SEM which generally surpasses an FIB device from the aspect of resolution.

Figure 17:
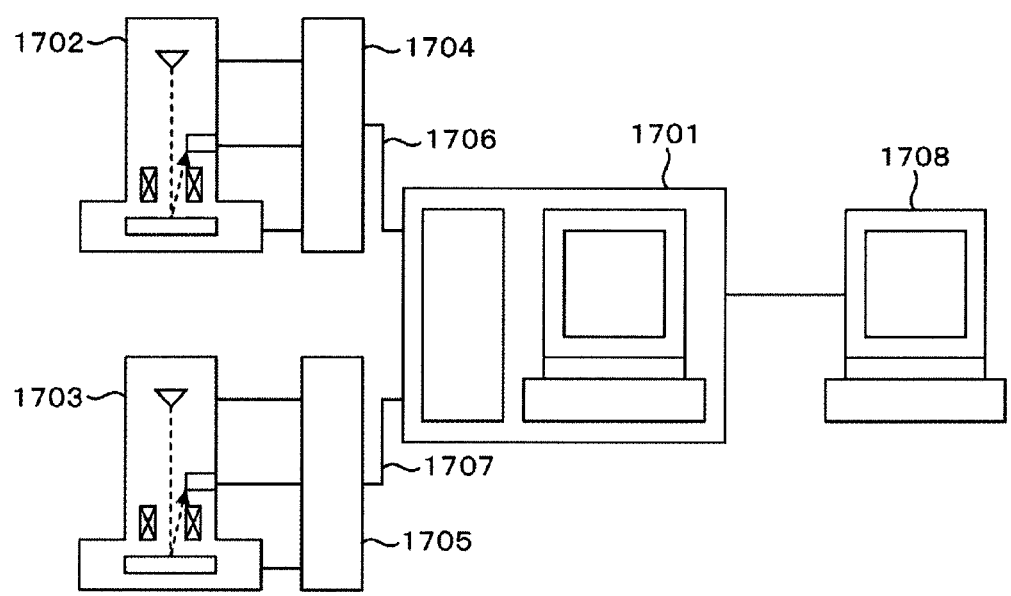
FIG. 17 is a diagram describing an example of a measurement system in which a plurality of SEM's are connected.

FIG. 17 exemplifies a system in which a plurality of SEM's are connected with a data management device 1701 at the center. In the case of the present embodiment, particularly, an SEM 1702 is one primarily for carrying out measurement and inspection of patterns of photomasks and reticles used in semiconductor exposure processes and an SEM 1703 is one primarily for measuring and inspecting patterns transcribed onto semiconductor wafers by exposure using the aforementioned photomasks or the like. Although the SEM 1702 and the SEM 1703 have no major differences in their basic constructions as electron microscopes, they have configurations in accordance with differences in size between semiconductor wafers and photomasks, respectively, or differences in tolerances against charge build-up.

To each of the SEM 1702 and the SEM 1703, respective control devices 1704 and 1705 are connected to perform control necessary for the SEM. In each SEM, while an electron beam emitted from an electron source is focused with lenses of several stages, the focused electron beam is scanned on a sample either in one dimension or in two dimensions with a scanning deflector.

Secondary electrons (SE) or backscattered electrons (BSE) emitted from the sample due to electron beam scanning are detected with a detector and are stored in a storage medium such as a frame memory in synchronism with the scan of the aforementioned scanning deflector. Also, the scan by the scanning deflector can be of arbitrary size, position, and direction and a scan for forming an image to be described later or a selective scan to edge portions can be taken.

The control and the like such as those described above are carried out in control devices 1704 and 1705 of respective SEM's and the images and signals acquired as the result of the electron beam scan are sent via communication lines 1706 and 1707 to the data management device 1701. Incidentally, in the present example, a description is given as if a control device controlling an SEM and the data management device performing measurements based on signals acquired by the SEM are separate entities, but it is not limited thereto; the control of the device and measurement processings may be devised to be carried out collectively in the data management device, or in each control device the SEM control and measurement processings may be carried out together.

Also, in the aforementioned data management device or control device, a program for executing measurement processings is stored and measurements or computations are carried out in accordance with the program. Moreover, in the design-data management device, design data of photomasks (hereinafter, may simply be called "masks") used in semiconductor manufacturing processes and wafers are stored. These design data are, for example, expressed in the GDS format or the OASIS format and are stored in prescribed forms. Incidentally, as for the design data, as long as software for displaying design data can display its format and can handle it as graphic data, the kind thereof is not concerned. Further, it is also acceptable to have a storage medium provided separately from the data management device store the design data in advance.

Also, a simulator 1708 is connected to the data management device 1701. In the simulator 1708, design data stored in an external storage medium or in the data management device 1701, a program generating a pattern layout based on semiconductor manufacturing process conditions and the like, and an arithmetic device executing the same are built in, and the layout data after simulation are configured to be able to be transferred to the data management device. Incidentally, in the present embodiment, a description is given regarding an example in which the simulation is carried out in the simulator 1708, but it is not limited thereto; the simulation may be carried out by executing the aforementioned program, for example, in the data management device 1708.

In addition, the data management device 1701 is provided with a function of generating the program (recipe) which controls the operation of the SEM based on semiconductor design data and functions also as a recipe settings part. Specifically, it sets the positions or the like for carrying out processings needed for the SEM such as desired measurement points, auto-focusing, automatic astigmatism correction, addressing points and the like on design data, pattern contour line data, and design data for which simulation has been performed, and creates a program based on the settings to automatically control the sample stage, the deflector, and the like of the SEM.

Also, as described later, the data management device 1701 is configured to store a database in which design data of semiconductor devices are registered or to be able to access design data stored in an external storage medium, and is configured so as to read out necessary data from a database according to arbitrary settings.

Figure 18:
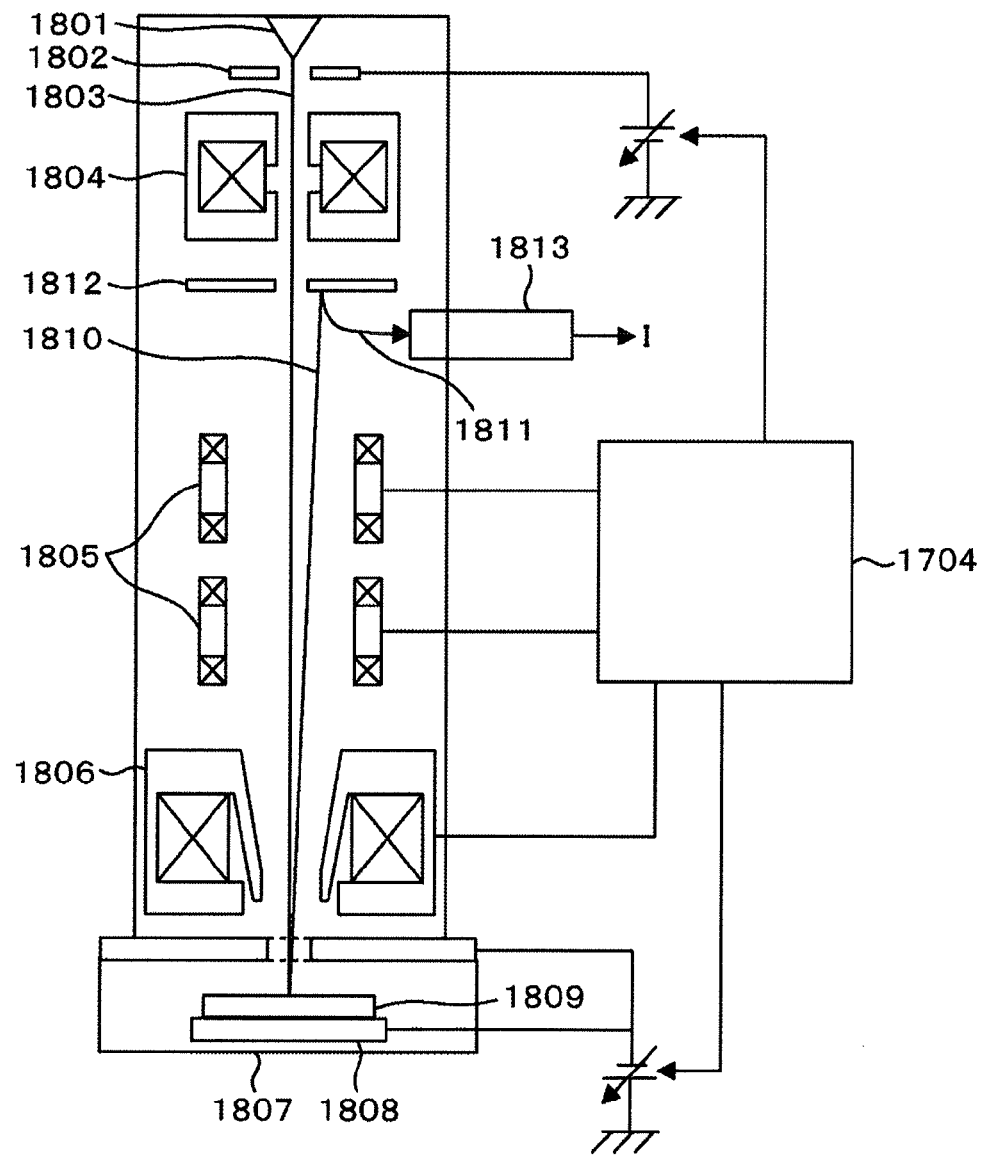
FIG. 18 is a schematic configuration diagram of a scanning electron microscope.

FIG. 18 is a schematic configuration diagram of a scanning electron microscope. An electron beam 1803, which is extracted from an electron source 1801 with an extraction electrode 1802 and accelerated with a not-illustrated acceleration electrode, is scanned in either a one-dimensional or two-dimensional manner on a sample 1809 with a scan deflector 1805 after being focused with a condenser lens 1804, which is a mode of focal lenses. The electron beam 1803 irradiates the sample 1809 along with being decelerated by a negative voltage applied to an electrode built in a sample stage 1808 and as being focused by the lens action of an objective lens 1806.

When the electron beam 1803 irradiates the sample 1809, electrons 1810 like secondary electrons and back-scattered electrons emitted from the irradiated spot. The emitted electrons 1810 are accelerated in the direction toward the electron source by the accelerating action due to the negative voltage applied to the sample and collide with a conversion electrode 1812 to generate secondary electrons 1811. The secondary electrons 1811 emitted from the conversion electrode 1812 are captured by a detector 1813 and, depending on the amount of captured secondary electrons, the output I of a detector 213 changes. According to this output I, the brightness of a not-illustrated display device changes. In the case of forming a two-dimensional image, for example, an image of a scan region is formed by attaining synchronization of the deflection signal to the scan deflector 1805 with the output I of the detector 1813.

Incidentally, in the example of FIG. 18, a description is given regarding an example in which electrons emitted from the sample are once converted at the conversion electrode to be detected, but, of course, it is not limited to such a configuration; it is possible, for example, to configure it so as to arrange an electron multiplier tube or a detection surface of a detector on the paths of the accelerated electrons.

The control device 1704, as well as controlling respective constituents of the scanning electron microscope, is provided with a function of forming an image based on detected electrons and a function of measuring pattern widths of patterns formed on the sample based on the intensity distribution of the detected electrons, which is called a line profile.

Figure 26:
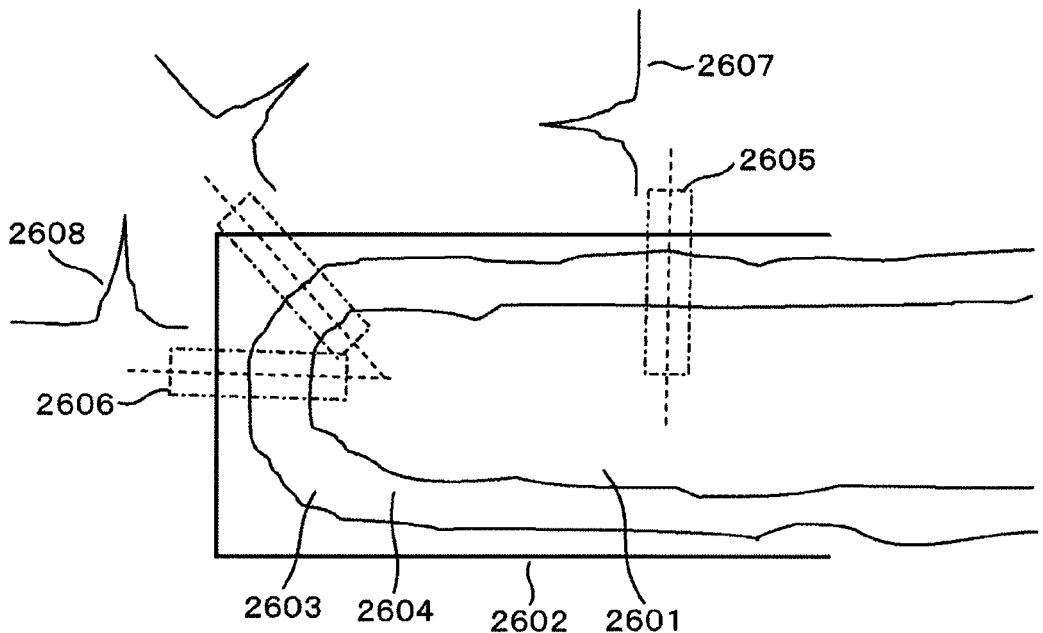
FIG. 26 is a diagram describing an example of a technique of extracting contour lines from a pattern image.
Figure 27:
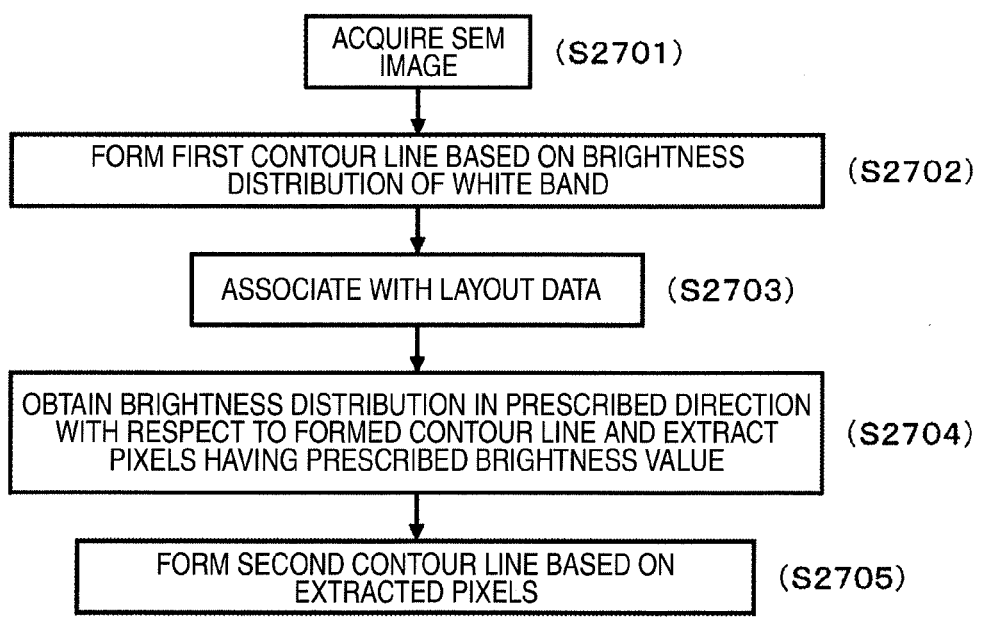
FIG. 27 is a flowchart describing a contour line extraction processing.

FIG. 26 is a diagram describing an example of a technique for extracting contour lines from a pattern image formed based on the detected electrons. Incidentally, this contour line extraction process may be devised to be carried out in the arithmetic device with which the data management device 1701 is equipped and it may also be devised to be carried out in the control devices 1704 and 1705 connected to the SEM's. In the contour line extraction, as exemplified in the flowchart of FIG. 27, an SEM image is formed first in the SEM 1702 or the SEM 1703 (Step 2701). Next, a first contour line 2604 is extracted (Step 2702) from a white band 2603 corresponding to an edge portion of a pattern 2601 on the SEM image. Incidentally, as an extraction technique for this first contour line 2603, conceivable is a method of extracting a pattern image composed of bit-map data from an SEM image and converting the same SEM image into pattern data composed of vector data.

Next, a superposition (Step 2703) of layout data 2602 and the first contour line 2604 is carried out by a vector data comparison of the formed first contour line 2604 and the layout data 2602 or by pattern matching. The layout data 2602 are line segment information of design data stored in the GDS format or the like. Upon carrying out such a superposition, regions for collecting the brightness distribution information are set perpendicular to the first contour line 2604 and brightness distributions 2607 and 2608 are detected (Step 2704). By extracting pixels having prescribed brightness in the brightness distribution formed in this way and defining their positions to be positions of a second contour line, formation of more accurate contour lines becomes possible (Step 2705).

Incidentally, as for such a technique for forming an accurate contour line, application of existing techniques described in JP-A-60-169977, JP-A-6-325176, JP-A-8-161508, JP-A-9-204529, and the like, is possible.

Moreover, by superposing the first contour line and the layout data as described above, association of the layout data and the first contour line in units of line segments becomes possible. By rendering the information about the respective line segments held by the layout data as the respective line segment information of the contour line, it becomes possible to register the contour line data in the same prescribed format as that of the design data.

Figure 2:
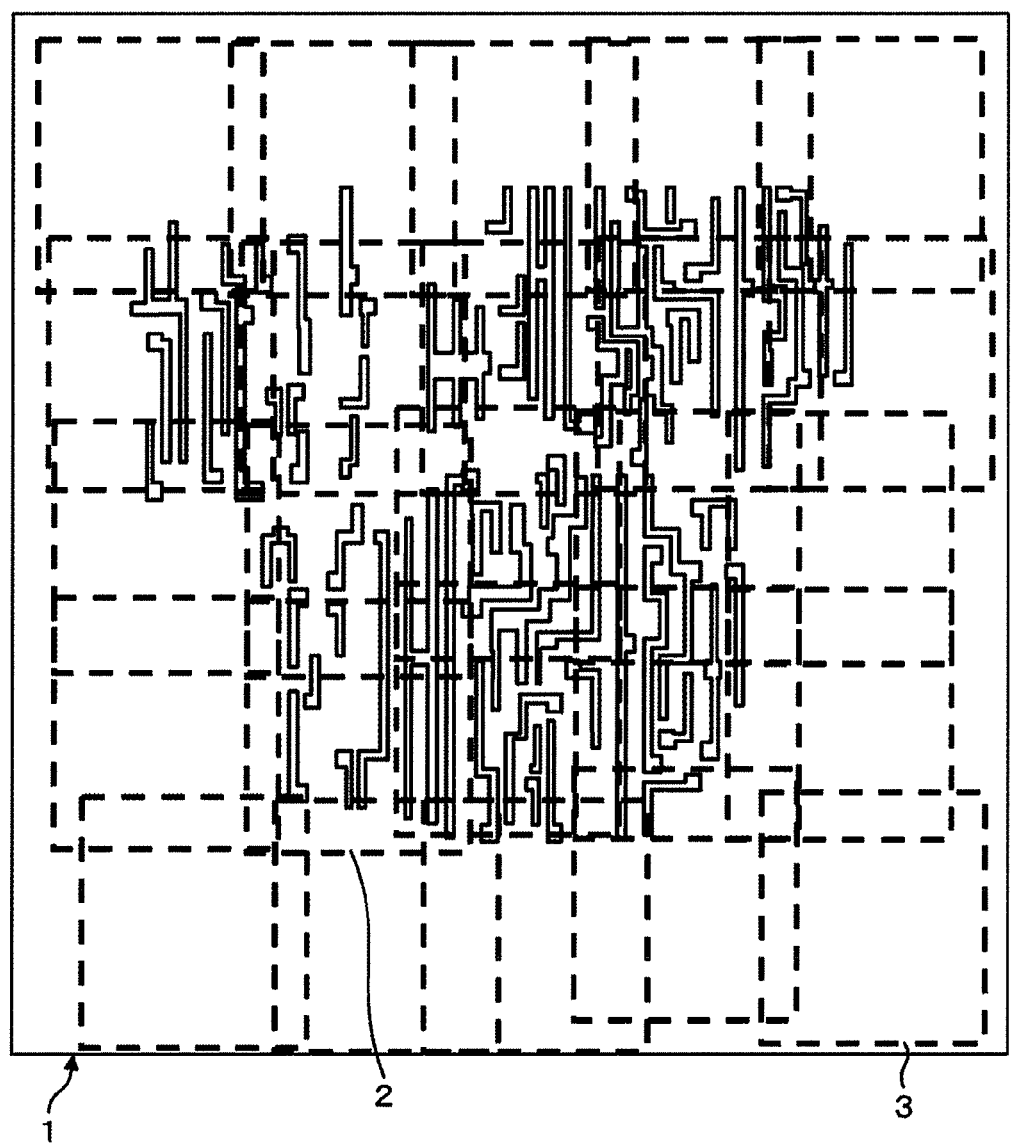
FIG. 2 is a diagram describing an example in which panorama image regions are set on the layout data.
Figure 28:
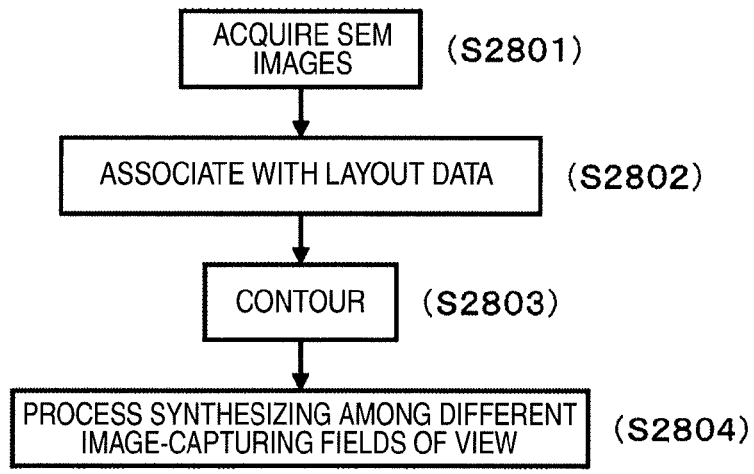
FIG. 28 is a flowchart describing an example of panoramization processing.

Also, in order to make it possible to acquire a synthesized image in which a plurality of image-capturing regions as expressed with dotted lines (25 image-capturing regions in the example of FIG. 2) are synthesized as exemplified in FIG. 2 so that a high-resolution image regarding a wide sample region can be formed, the recipe is so programmed as to acquire a plurality of positions for image capture. FIG. 28 is a flowchart describing the processes carrying out synthesis of a plurality of images (hereinafter, may also be called as panoramization). First, in accordance with image acquisition conditions set in advance, images of a plurality of positions are acquired (Step 2801). Next, association with layout data is carried out and contouring is performed (Steps 2802 and 2803). By synthesizing contour lines of image-capturing regions at a plurality of positions, which are formed as described above, panoramization is executed (Step 2804). In order to execute panoramization such as this, overlaid regions are provided with respect to a plurality of image-capturing regions and a synthesis between the image-capturing regions is carried out so that patterns formed across two image-capturing regions overlap.

Hereinafter, a description is given regarding a technique of executing contouring with high efficiency in a device capable of executing contouring as exemplified above and panoramization processing.

1. Description of a First Technique of Making Contouring Processing Steps More Efficient First, when panoramization such as mentioned above is executed, contouring processings are repeatedly carried out on the same pattern regions in overlapped portions among a plurality of images. In the present embodiment, a description is given of a technique of implementing an improvement in the efficiency of measurement and inspection processings by eliminating such duplicate processings and executing contouring selectively.

Figure 1:
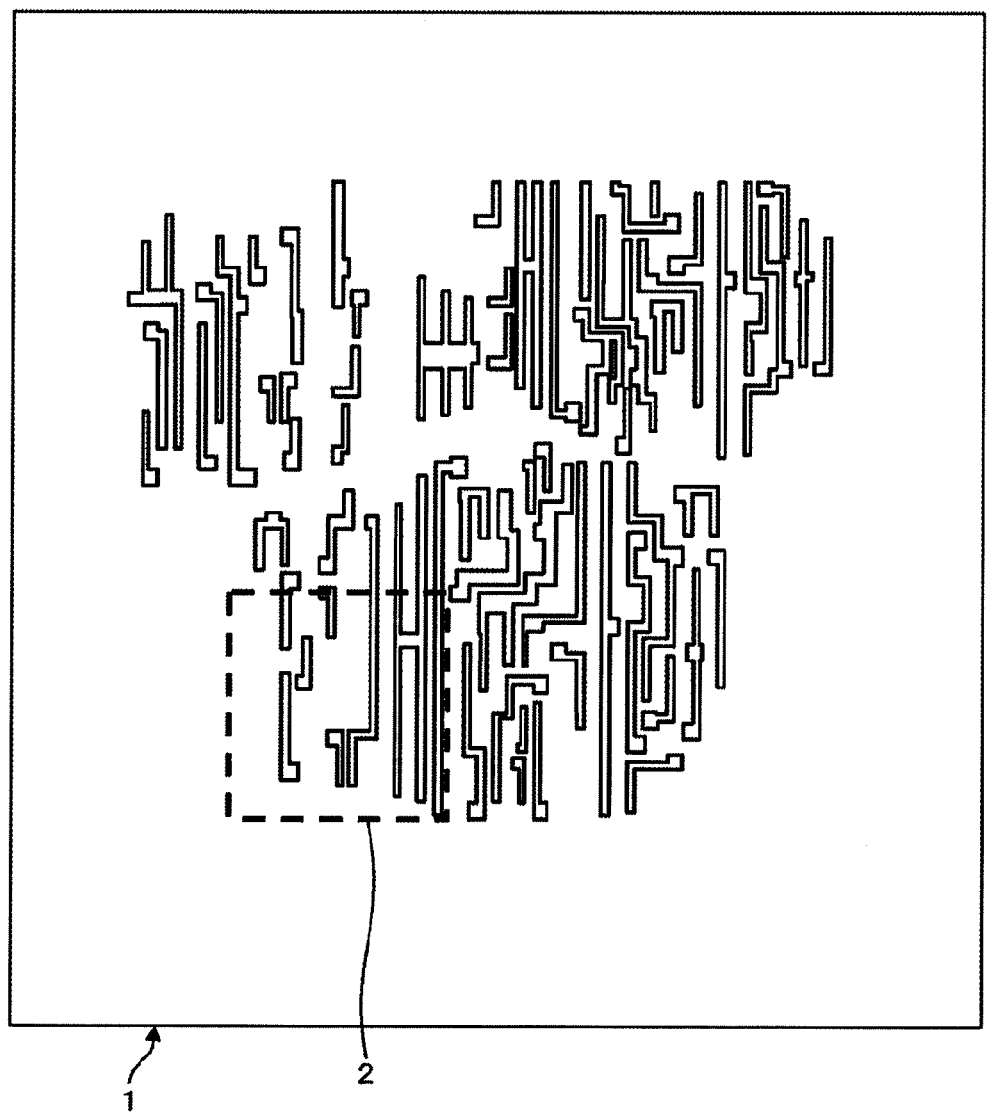
FIG. 1 is a diagram describing an example of pattern regions set on layout data and an image-capturing region.

FIG. 1 is a diagram describing an example of layout data. Image acquisition positions are selected on such layout data and a recipe is set for actually carrying out image capture by an SEM based on the selection. FIG. 1 exemplifies a pattern region 1 where defect detection and measurement are conducted and an image-capturing region 2 where images within the pattern region are acquired. FIG. 2 is a diagram describing an example in which the image-capturing region 2 and another image-capturing region 3 are set on the layout data to panoramize the image-capturing region 2 and its surrounding regions. When the image-capturing region 2 is optimized in the pattern region 1, a file in which position information of image-capturing points and pattern information is included is generated. Also, it is set up so that the same pattern is captured across a plurality of images as information for generating a synthesized image.

Based on the image acquisition conditions set as mentioned above, image acquisition is carried out regarding each of the image-capturing regions of a wafer set inside a charged particle beam device and contour lines are extracted from the images. Using the contour lines acquired in such a manner the pattern dimensions are measured and it is determined whether there is a defect by a comparison with a predetermined tolerance of a pattern size.

Since it takes an appreciable time until a defect is detected if images are captured at all image-capturing locations, it is possible to carry out image acquisition efficiently by integrating into the recipe an algorithm devised to automatically skip image capturing for an image-capturing region 3 located in the lower right part in which no pattern is included and the like even among the image-capturing regions set as shown in FIG. 2, for example. Further, to design to make the contouring processing efficient, after acquiring images at the image-capturing points and when contour lines of a pattern included within the images are extracted, the overlapped portions are compared and the contour lines of only the minimum required images are extracted from file information about the plurality of images in the case where the pattern is included in a plurality of images.

Figure 3:
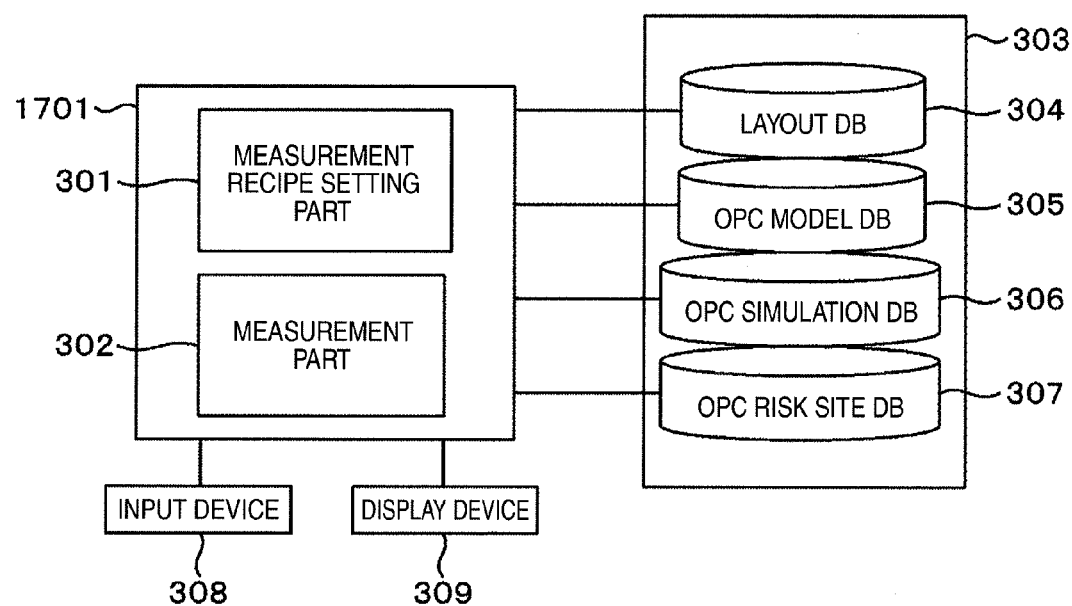
FIG. 3 is a diagram describing an example of a setting device which sets contour line extraction conditions.

A device configuration for carrying out such a processing is exemplified in FIG. 3. Incidentally, although in the present embodiment the data management device 1701 exemplified in FIG. 17 is described as a device executing a program for carrying out efficient processing of contouring, it is not limited thereto and it is also possible to carry out the processing described below with another computer or the like.

The data management device 1701 is provided with a measurement recipe setting part 301 and a measurement part 302; the measurement recipe setting part 301 is configured so as to primarily generate recipes using design data of semiconductor devices and the like and the measurement part 302 is configured so as to primarily execute data processings based on acquired SEM images. Also, the data management device 1701 is configured to be able to access the design data stored in an internal or external storage medium and has a configuration in which reading and writing of data as needed are possible. A design database 303 is provided with a layout database 304 memorizing layout design data (CAD data or the like) of semiconductor patterns, an OPC model database 305 memorizing design data of mask patterns for which OPC (Optical Proximity Correction) processing is conducted based on layout data and the like, an OPC simulation database 306 memorizing pattern profiles obtained by conducting OPC simulations, and an OPC risk site database 307 memorizing information on OPC risk sites specified by the OPC simulations.

As for the types of design data stored in the design database 303, it is acceptable as long as it is in a format capable of displaying figures based on the design data (for example, pattern contours) with software for displaying images used in the data management device 1701 or the like. Also, the design data are those converted from circuit design data and have relations with the circuit design data; it is specified in advance to which signal transmission path on the circuit design data a specific figure on the pattern layout corresponds.

The data management device 1701 is provided with: an input/output interface for transferring data and signals to and from not-illustrated external devices, a ROM storing programs regarding to inspection and analysis of a semiconductor wafer, constants necessary for processings, and the like, an arithmetic part carrying out various kinds of arithmetic processings, a RAM temporarily storing arithmetic results, data during computation, and the like, a storage part storing various data, and the like; it is provided with a display device 309 such as a monitor and an input device 430 such as a keyboard or a pointing device.

The data stored in the OPC simulation database 306 are stored information of the OPC model database 305 and information obtained by simulating the pattern profiles formed on the wafer after exposure based on used exposure machines, exposure conditions, and the like. Further, from the simulation results, information pertaining to a spot for which a discrepancy in a profile between a predicted profile of a pattern and a design data exceeds a threshold value is stored in the OPC risk site database 307. Such a simulation may be carried out in an external simulator 1708 exemplified in FIG. 17 or may also be conducted by executing a prescribed program in the data management device 1701.

In the measurement recipe setting part 301, SEM image acquisition conditions of an externally connected SEM or acquisition conditions of measurement results are set based on designation from the input device 308 or the like. Specifically, coordinates of an acquired image, a pixel size, a beam diameter, a beam accelerating voltage, a threshold value for a detected secondary voltage, and the like are set and stored in a prescribed storage medium.

Figure 4:
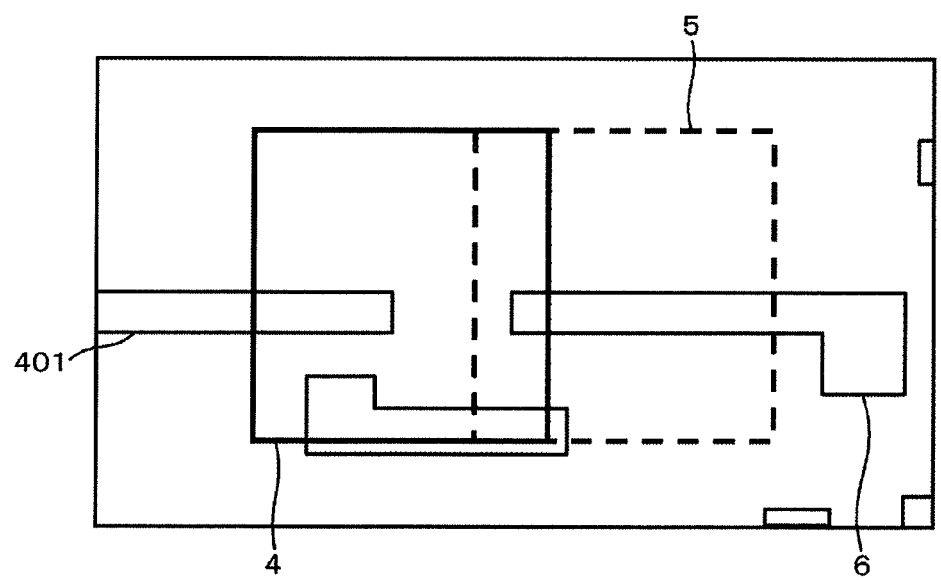
FIG. 4 is a diagram describing an example in which two image-capturing regions are set while an overlaid region on the layout data is provided.

In the data management device 1701, an efficient processing of contouring as described below is carried out. FIG. 4 is a diagram describing a process of setting image-capturing regions on the layout data. In the present embodiment, a description is given regarding an example in which an image-capturing region 4 and an image-capturing region 5 are set on layout data including a pattern 6 while an overlaid region is provided.

Figure 5:
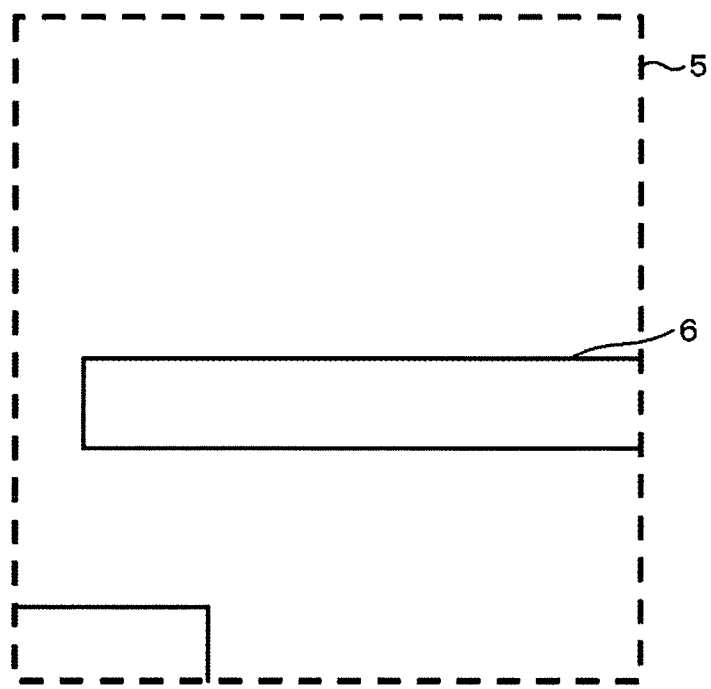
FIG. 5 is a diagram for which one of the two image-capturing regions exemplified in FIG. 4 is enlarged.
Figure 6:
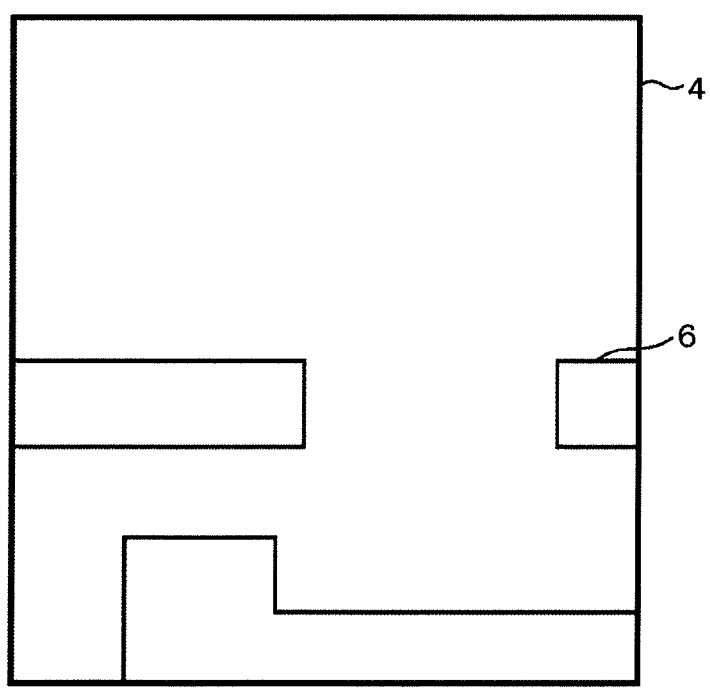
FIG. 6 is a diagram for which the other of the two image-capturing regions exemplified in FIG. 4 is enlarged.

In the example of FIG. 4, the image-capturing region 4 and the image-capturing region 5 overlap with a part of an identical pattern 6. FIG. 5 is an enlarged view of the image-capturing region 5 and FIG. 6 is an enlarged view of the image-capturing region 4.

In this case, according to the pattern information of the image-capturing region 4 and the pattern information of the image-capturing region 5, the pattern of the image-capturing region 5 is selected which has more information of the identical pattern other than the overlapping information. Namely, contour line extraction of the pattern 6 is conducted in the image-capturing region 5 shown as enlarged in FIG. 5 and contour line extraction of the pattern 6 is not conducted in the image-capturing region 4 shown as enlarged in FIG. 6.

Figure 7:
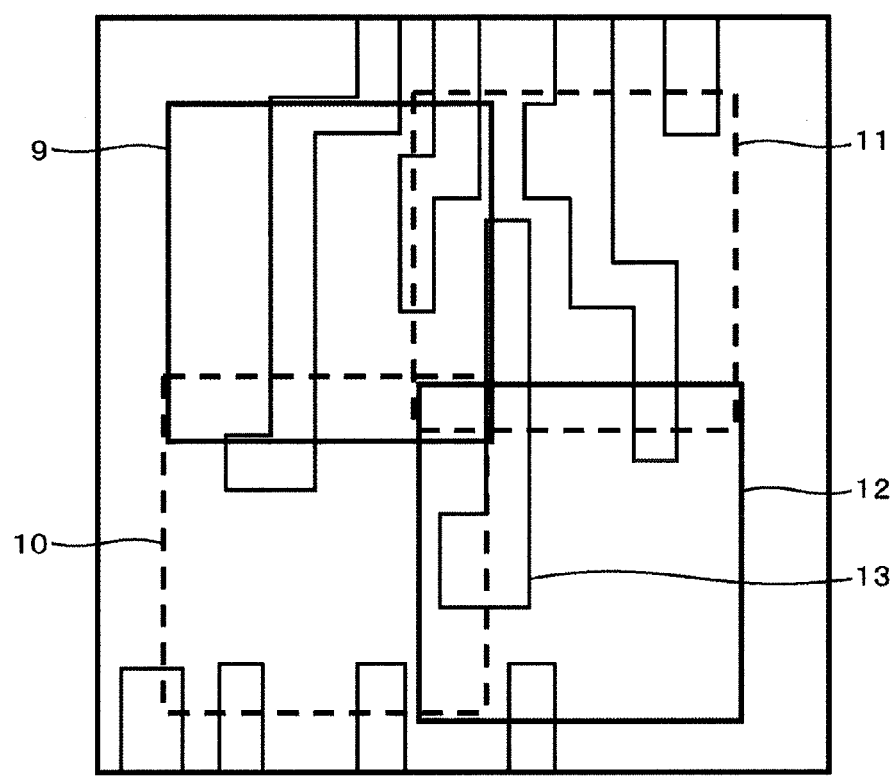
FIG. 7 is a diagram describing an example in which four image-capturing regions are set while image-capturing regions on the layout data are provided.
Figure 8:
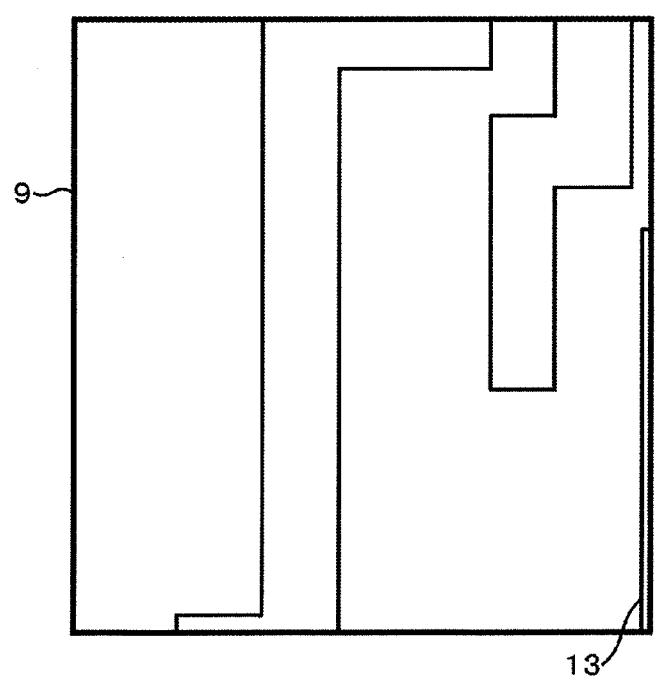
FIG. 8 is a diagram for which a first image-capturing region out of the four image-capturing regions exemplified in FIG. 7 is enlarged.
Figure 9:
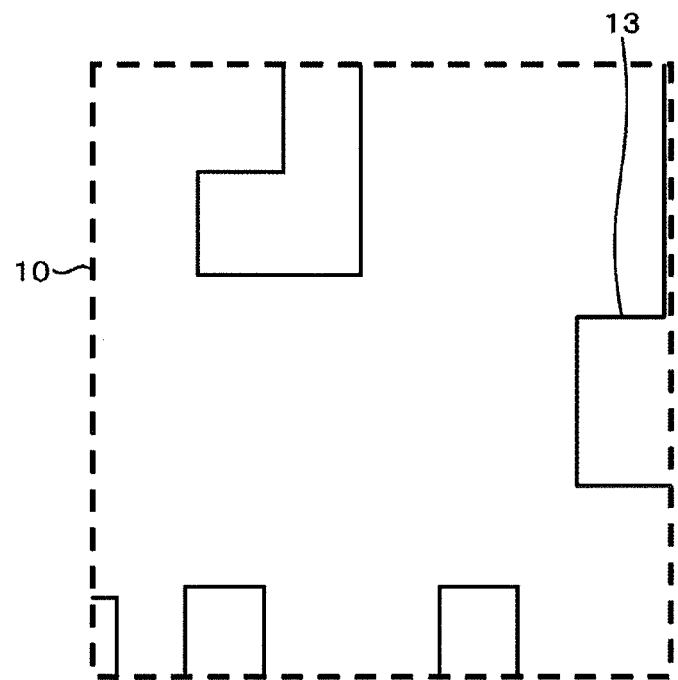
FIG. 9 is a diagram in which a second image-capturing region out of the four image-capturing regions exemplified in FIG. 7 is enlarged.
Figure 10:
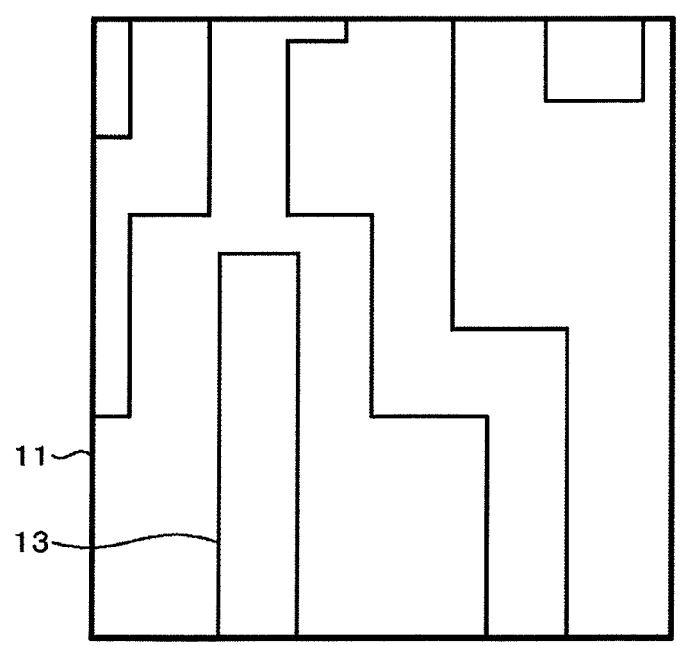
FIG. 10 is a diagram in which a third image-capturing region out of the four image-capturing regions exemplified in FIG. 7 is enlarged.
Figure 11:
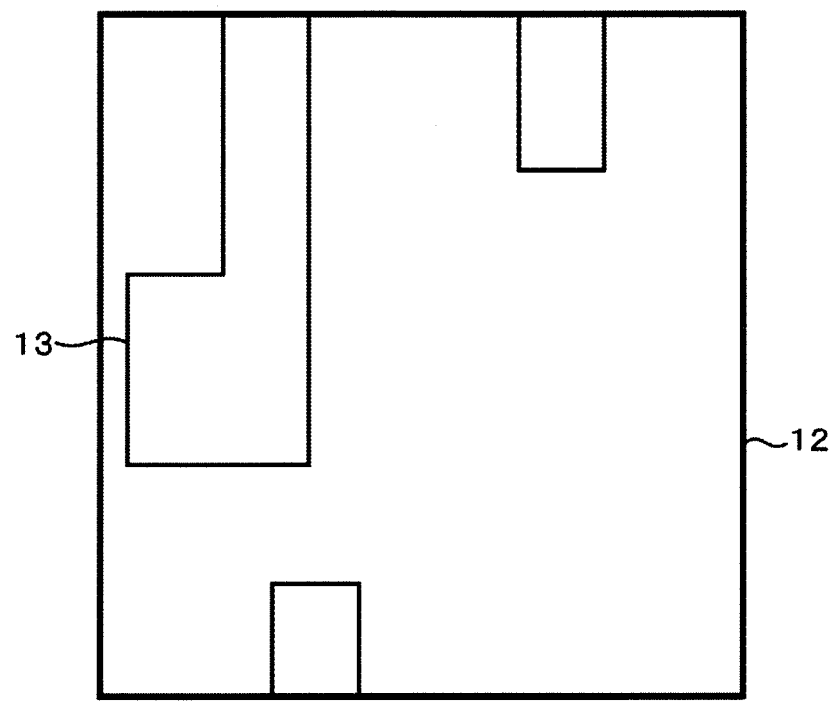
FIG. 11 is a diagram in which a fourth image-capturing region out of the four image-capturing regions exemplified in FIG. 7 is enlarged.

Also, in the case of FIG. 7, in an image-capturing region 9, an image-capturing region 10, an image-capturing region 11, and an image-capturing region 12, a pattern 13 is duplicated. In this case, the contour line extraction conditions are determined based on the pattern information of the pattern 13 in the respective regions. More specifically, occupied regions of the pattern 13 in the respective regions are compared with each other and contouring of the pattern 13 is selectively executed as for the image-capturing region of the largest occupied area. In the example of FIG. 7, the image-capturing region of the largest area of the pattern 13 is the image-capturing region 12 shown as enlarged in FIG. 11. Accordingly, regarding the line segments of the pattern 13 present in the image-capturing region 12, contouring is executed selectively in the image-capturing region 12, without carrying out contouring in the image-capturing regions 9, 10, and 11 (shown as enlarged in FIG. 8, FIG. 9, and FIG. 10, respectively).

Next, contouring is executed regarding the portion of the pattern 13 that is not covered in the image-capturing region 12. In this case, the image-capturing regions covering the portion of the pattern 13 belonging outside the image-capturing region 12 are the image-capturing region 9 and the image-capturing region 11. Regarding both of these, the areas to which the pattern 13 belongs are compared and selective contouring of the pattern 13 is executed regarding the image-capturing region 11 of the larger area.

By determining the image-capturing regions that should be contoured based on a prescribed standard as mentioned above, it becomes possible to intend an improvement of the contouring processing efficiency. Also, in the present embodiment, in regions other than the overlapping portions of the image-capturing regions, contouring is executed selectively regarding the image-capturing region of a relatively large occupied area of a pattern, and with such the selective contouring it becomes possible to fit one pattern into one image-capturing region as much as possible. Namely, for one pattern, it becomes possible to form contour lines having few joints among image-capturing regions.

Incidentally, since the data of the pattern area are written in advance into the design data, the data management device 1701 can look up the data to derive therefrom the area of the pattern other than the overlaid region. Also, the pattern area inside the image-capturing region can be obtained by counting the number of pixels of the pattern existing inside the frame specifying the image-capturing region.

Figure 12:
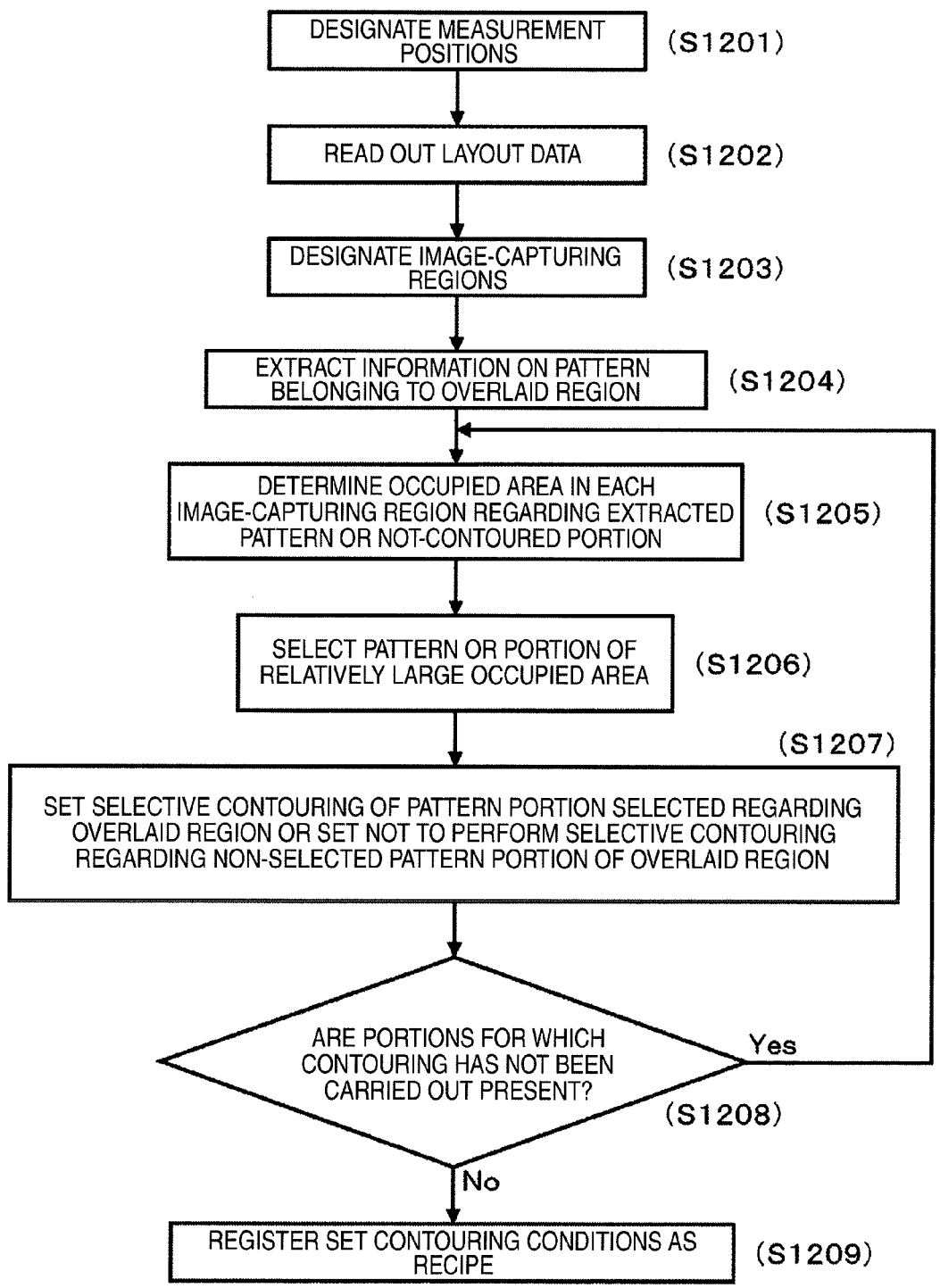
FIG. 12 is a flowchart describing processes for determining image-capturing regions in which contouring is carried out.

FIG. 12 is a flowchart describing the processes during determining the image-capturing regions to conduct contouring. First, the measurement positions on the layout data are designated (Step 1201). Here, based on the settings of the coordinates of the measurement region, the size of the region, or the magnification of the image, the two-dimensional region needed for measurement is set. Next, the layout data of the portion are read out (Step 1202). Next, on the read-out layout data, m×n image-capturing regions are set (Step 1203). In this process, a plurality of image-capturing regions to be panoramized are selected. Incidentally, in this process a plurality of image-capturing regions may be set on a GUI (Graphical User Interface) screen as described later or a plurality of image-capturing regions may be allocated automatically in accordance with a prescribed rule with reference coordinates as the center. Meanwhile, one image-capturing region is a region for which a Field of View (FOV) of a scanning electron microscope is allocated.

Next, the information about the pattern belonging to the overlaid region is extracted from the layout data (Step 1204). Regarding the pattern extracted in this way, the occupied area for each image-capturing field of view to which it belongs is determined (Step 1205) and among the plurality of image-capturing fields of view the image-capturing region of the largest occupied area is selected (Step 1206). Image processing conditions are set so that the pattern belonging to the selected image-capturing region is contoured or so that contouring of the pattern belonging to image-capturing regions that were not selected is not executed selectively (Step 1207). Regarding a pattern that is not included in the overlapping portion, setting is conducted to execute normal contouring.

Next, it is judged whether there exists a pattern portion that is not included in the image-capturing region of the largest occupied area (Step 1208); in the case where the pattern portion exists, a judgment on the sizes of the occupied areas as described above is carried out regarding the image-capturing regions to which the pattern portion belongs, and an image-capturing region that should be contoured is selected. According to the example of FIG. 7, among the four image-capturing regions 9, 10, 11, and 12 to which the pattern 13 belongs, setting of selectively contouring the portion of the pattern 13 belonging to the image-capturing region 12 of the largest occupied area is carried out first; then, regarding the portion of the pattern 13 existing outside the image-capturing region 12, setting for selectively carrying out contouring with respect to the pattern 13 regarding the image-capturing region 11 for which it is judged that the occupied area is largest is carried out. The contouring conditions set as above are registered as a recipe controlling image processings during image acquisition (Step 1209).

According to processings as exemplified in FIG. 12, it becomes possible to carry out appropriate contouring setting even in a case where one pattern extends over a plurality of image-capturing regions.

Figure 29:
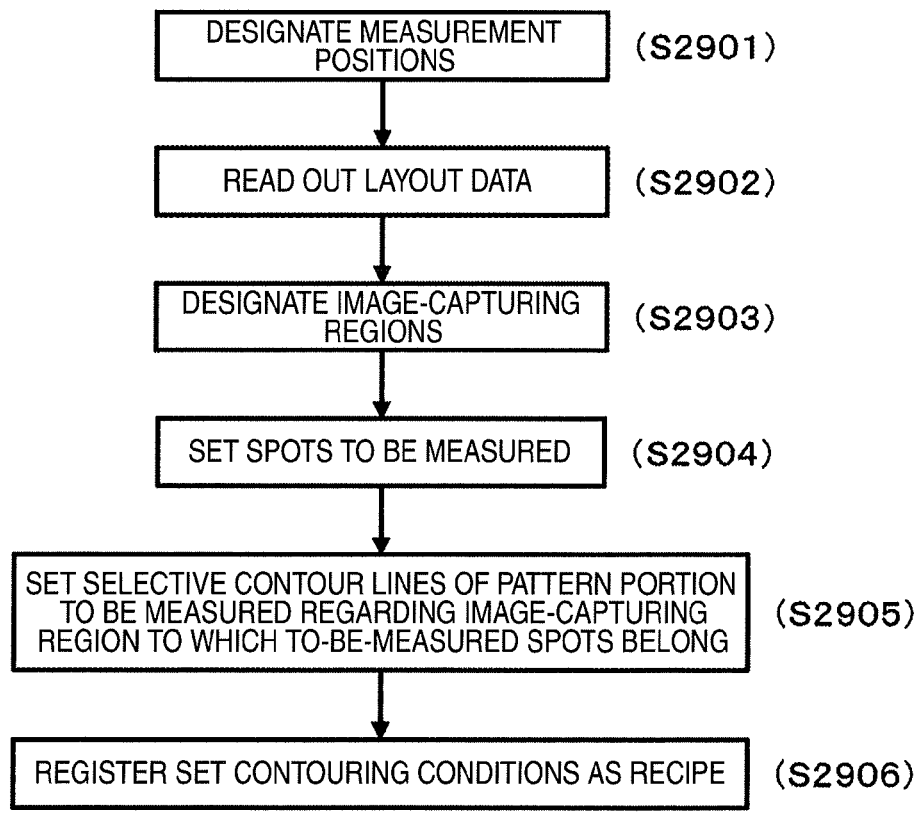
FIG. 29 is a flowchart describing processes of setting a contouring region on layout data.

Incidentally, in the present embodiment, a description of a technique is given in which the image-capturing regions to be contoured are determined based on the pattern areas within the image-capturing regions; in the case of carrying out measurement between the line end of the pattern 6 and the line end of a pattern 401 of FIG. 4, it may be devised that contouring is carried out in preference to the side of the image-capturing field of view 4 regarding the pattern 6. FIG. 29 is a flowchart describing the process of determining setting conditions. Since Step 2901 to Step 2903 are the same as those in the flowchart exemplified in FIG. 12, a description thereof is omitted.

In the flowchart exemplified in FIG. 29, the spots to be measured (coordinate information for specifying line segments of patterns including a measurement starting point and a measurement end point or a line segment of a pattern to be measured) are selected on the design data for which an image-capturing region is set (Step 2904). An image-capturing region to which the spots to be measured set in this way belong is set as the region to be contoured (Step 2905). The contouring conditions set as described above are registered as a recipe controlling image processings during image acquisition (Step 2906).

According to processings as exemplified in FIG. 29, it becomes possible to carry out appropriate contouring setting even in the case where spots to be measured lie across a plurality of image-capturing regions. Namely, since the spots to be measured can be fit in one image-capturing region, it becomes possible to exclude as much as possible states where the spots to be measured lie across a plurality of image-capturing regions.

Figure 20:
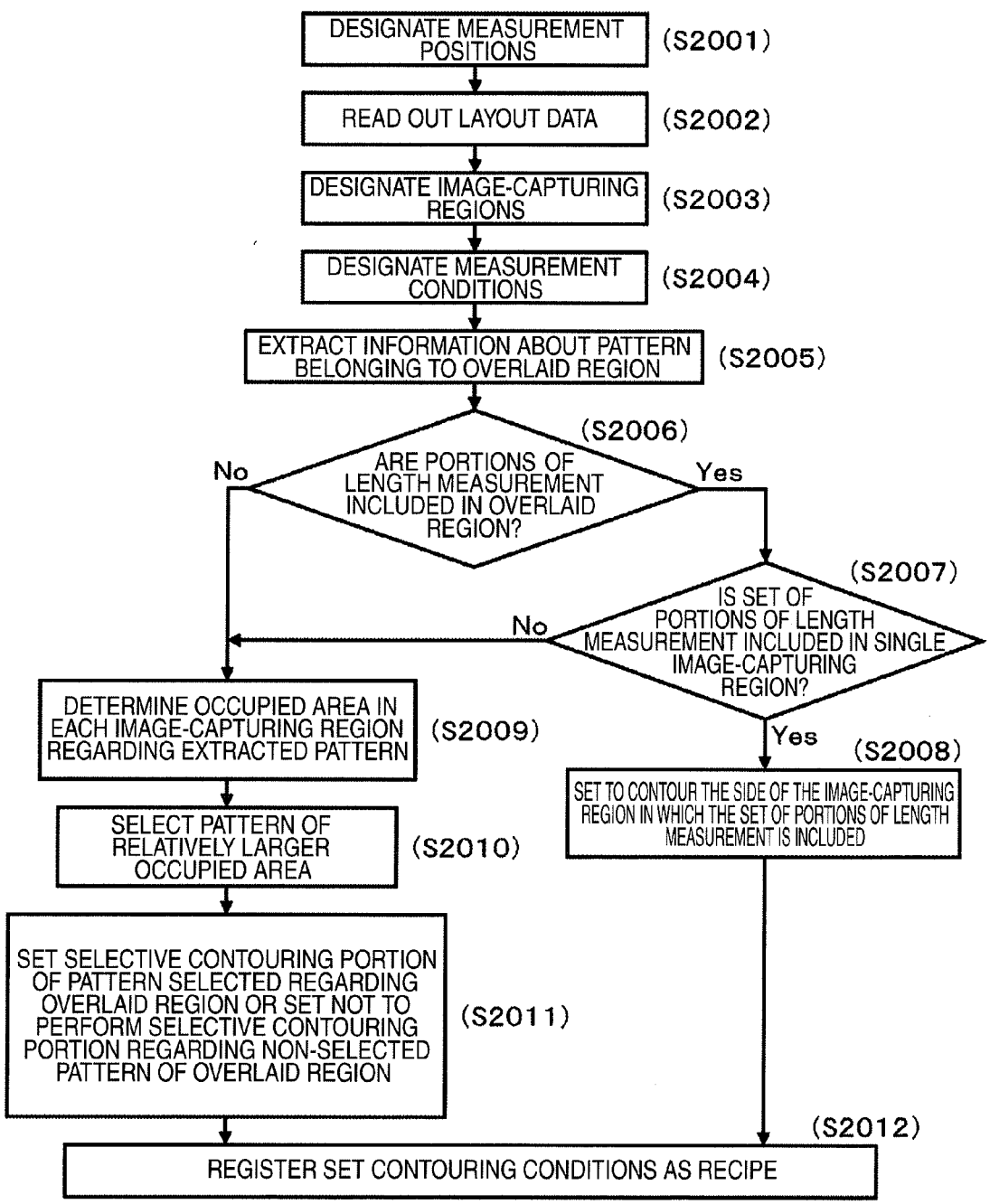
FIG. 20 is a flowchart describing processes of setting a contouring region on layout data.

Also, FIG. 20 is a flowchart describing condition setting process into which the contouring condition setting process exemplified in FIG. 12 and the contouring condition setting process exemplified in FIG. 29 are combined. Step 2001 to Step 2004 are substantially the same as Step 2901 to Step 2904 of FIG. 29. In the flowchart of FIG. 20, it is judged whether portions of length measurement are included in an overlapping region (Step 2006) and, when it is judged that a set of portions of length measurement (a measurement starting point and a measurement end point) is included in a single image-capturing region (Step 2007), it is set to contour the pattern belonging to the image-capturing region in which the set of portions of length measurement is included (Step 2008); otherwise, image-capturing regions to be contoured are set (Step 2009 to Step 2011) depending on the size of the pattern based on the same way of thinking as in the flowchart of FIG. 12. The contouring conditions set as above are registered as a recipe controlling image processings during image acquisition (Step 2012).

In the flowchart exemplified in FIG. 20, it is first judged whether the spots to be measured are included in an overlapping region and whether the spots to be measured are included in a single image-capturing region; if the spots appear to be included, in preference to measurement accuracy of the spots to be measured, conditions are set to carry out contouring in the image-capturing region on the side in which the spots to be measured are included. And, in the case where a set of portions of length measurement is not included in a single image-capturing region, setting of the contouring conditions is carried out based on the occupied area of the pattern. According to such the processes, it becomes possible to eliminate influences such as errors of joining between image-capturing regions on the length measurement results during length measurement.

Figure 13:
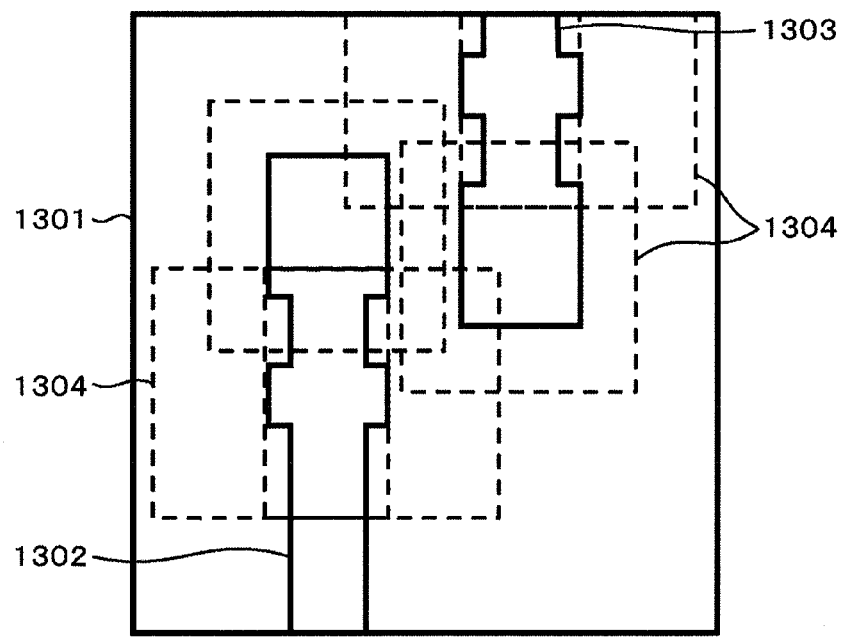
FIG. 13 is a diagram describing an example of setting contouring regions on design data.
Figure 19:
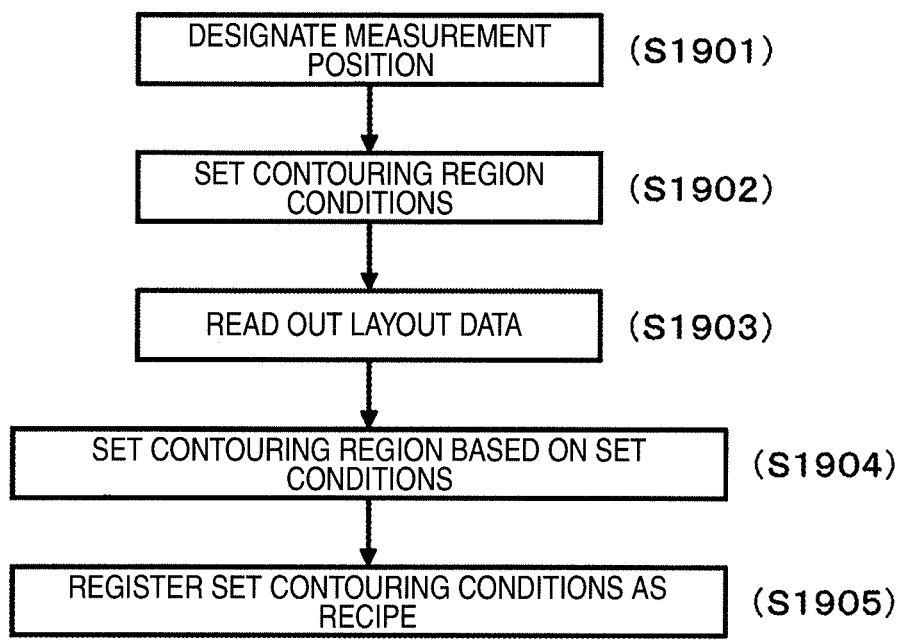
FIG. 19 is a flowchart describing processes of setting a contouring region on layout data.

2. Description of a Second Technique of Making Contouring Processing Steps More Efficient FIG. 13 is a diagram describing an example of a technique designed to make measurement and inspection efficient by selectively carrying out contouring regarding necessary portions and not executing contouring processing regarding other portions in a pattern region 1301. In the present embodiment, conditions are set for conducting contouring selectively regarding either the portions to be measured and inspected or the portions and their surrounding regions. FIG. 19 is a flowchart describing the processes. First, a measurement position (measurement region 1301) on the layout data is designated (Step 1901). Next, the contouring region conditions are set (Step 1902). Here, for example, types of patterns and information on a region centered at the coordinates of the patterns are set.

Next, the layout data of the portions are read out (Step 1903). Next, the contouring regions are set on the read layout data based on the setting conditions of Step 1902. In the example of FIG. 13, regions with prescribed sizes centering the OPC patterns of patterns 1302 and 1303 for which OPC processings have been conducted (region 1304) are set as contouring regions.

Figure 14:
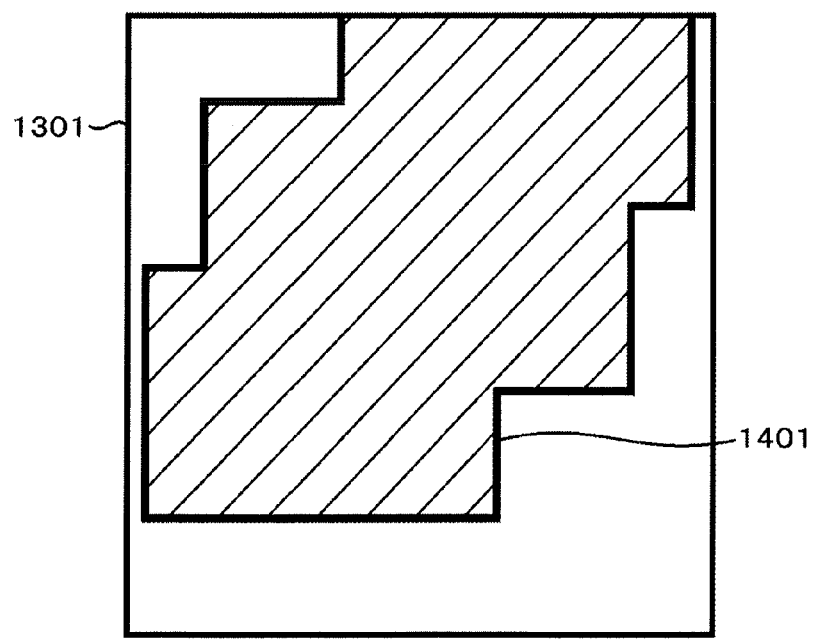
FIG. 14 is a diagram describing an example of setting contouring regions on design data.

There is a possibility that the influence due to the optical proximity effect is exercised not only on the patterns to be measured but also on their surroundings. Accordingly, by verifying a region of a prescribed size taking the OPC pattern coordinates as a reference, verification of the suitability of the OPC pattern becomes possible. As exemplified in FIG. 14, by rendering an region including a plurality of regions 1304 to be a contouring region 1401 to carry out selective contour line formation, it becomes possible to implement an improvement of the efficiency of the contouring processings in addition that measurements that are in agreement with the objectives of measurement such as verification of the OPC pattern become possible. Also, since unnecessary measurement is not carried out, there are also effects on improvement in the measurement efficiency and reduction of the amount of data. Incidentally, from the viewpoint of the improvement in the measurement efficiency, a technique is conceivable to carry out contouring in all image regions and carry out measurement selectively within the contouring region 1401.

The contouring conditions set as above are registered as a recipe controlling image processings during image acquisition (Step 1905).

Figure 15:
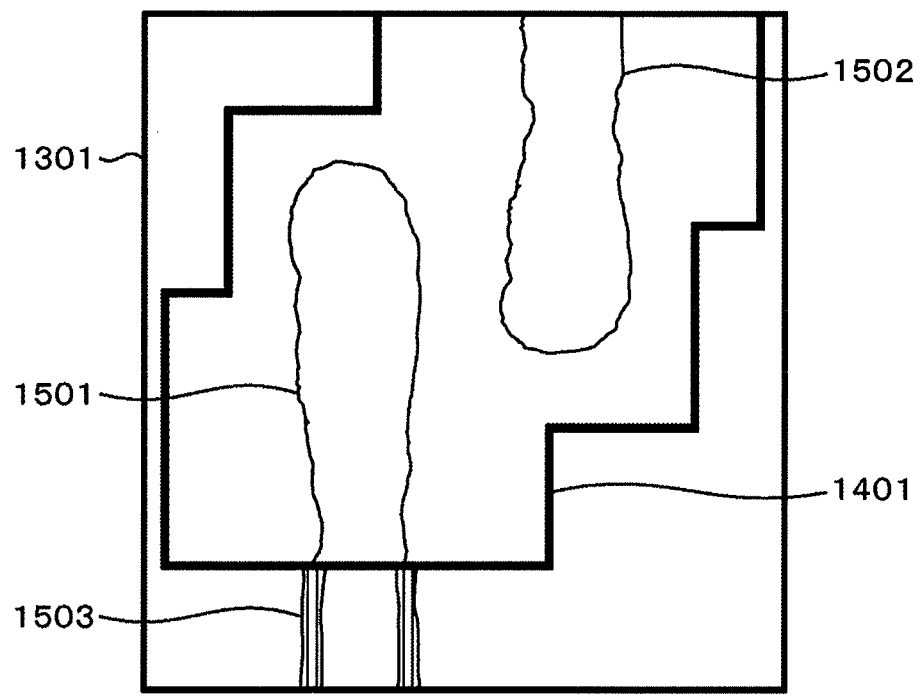
FIG. 15 is a diagram describing an example in which edges within a set contouring region are selectively contoured with respect to an SEM image.
Figure 21:
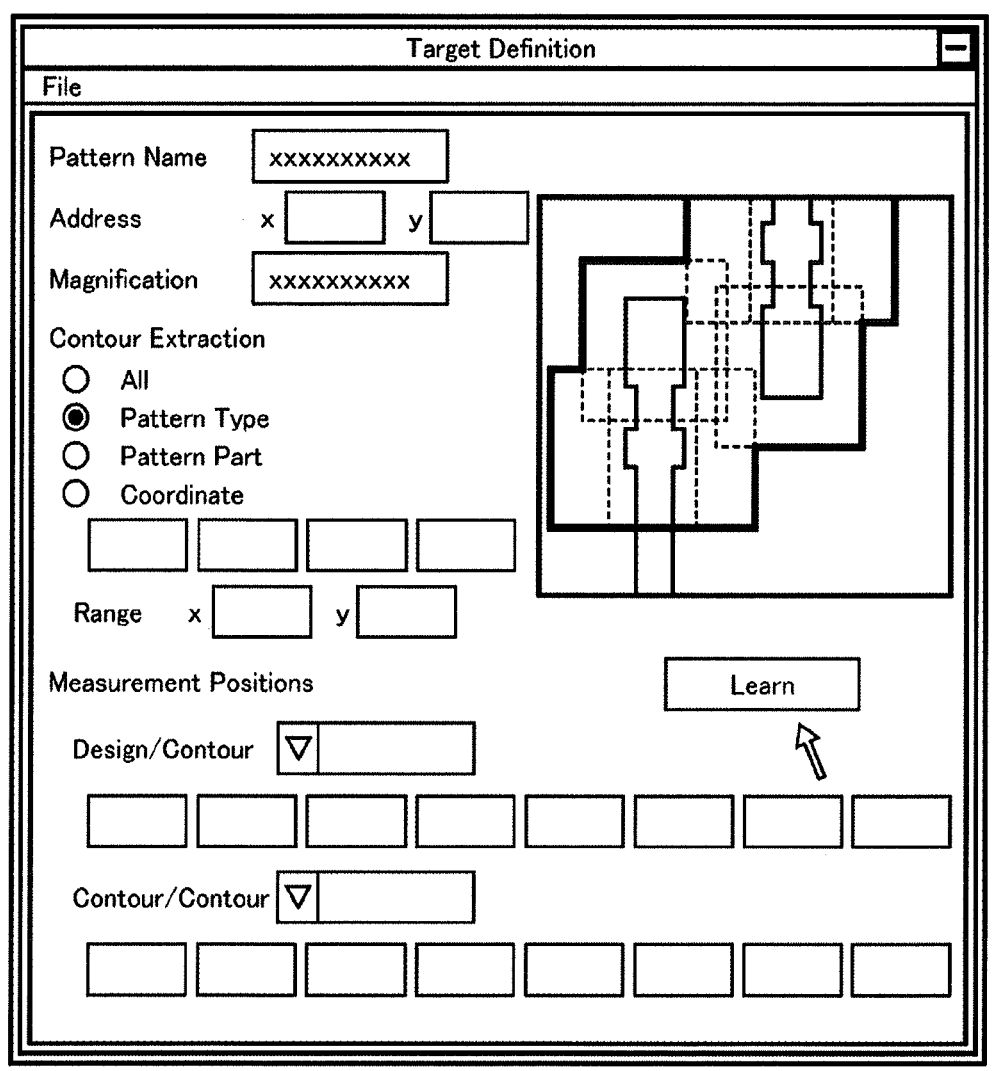
FIG. 21 is a diagram describing an example of a GUI screen for setting a contouring region.

FIG. 15 is a diagram describing an example of an SEM image in which selective contouring is carried out based on a set recipe. In image data 1504, contouring is executed regarding pattern edges included in the contouring region 1401 with a technique such as exemplified in FIG. 26, for example, and contour lines 1501 and 1502 are formed. An edge 1503 is the portion for which contouring processing is not carried out. FIG. 21 is a diagram describing an example of a GUI screen for designation of measurement positions carried out in Steps 1901 and 1902 of FIG. 19 and for setting of contouring region conditions. By designating a name of a pattern or a region in which a pattern is present ("Pattern Name"), coordinates where a pattern is present ("Address"), the size of an image that is actually acquired ("Magnification"), and the like on this screen, an operator designates information pertaining to the measurement region. The setting of contouring conditions is carried out in the "Contour Extraction" portion. When "All" is selected in the contouring condition setting, setting is carried out such that the edges included in the measurement region are contoured without omission. Also, by selection of "Pattern Type", "Pattern Type", and "Coordinate" and designation of "Range", a position serving as a reference for executing contouring and a contouring range with the position as a reference are set. For example, when an OPC pattern having certain characteristics is selected in "Pattern Type", and a range is decided upon in "Range", a range with the coordinates of the OPC pattern as a reference is set and the portion is set as a contouring region. Also, in "Pattern Type" setting of general patterns such as lines and holes, types of patterns constituting semiconductor devices such as gates and diffusion layers, and the like may be enabled additionally. Further, in the column of "Pattern Part" it is desirable to make selection of pattern portions possible. As an example thereof, an end part of a pattern ("Line End"), "Inner Corner" or "Outer Corner" that indicates a bent part of a pattern, or the like is conceivable, for example. By enabling setting of a range ("Range") rendering such pattern portions as a reference, setting for verifying relationships between pattern profiles and the optical proximity effects becomes possible. Additionally, it is acceptable to carry out setting of contouring regions based on coordinate information ("Coordinate") and range setting ("Range"). Further, more than one of "Pattern Type", "Pattern Type", "Coordinate", and the like may be selected; it is acceptable to decide the contouring regions based on the multiple selections.

Figure 16:
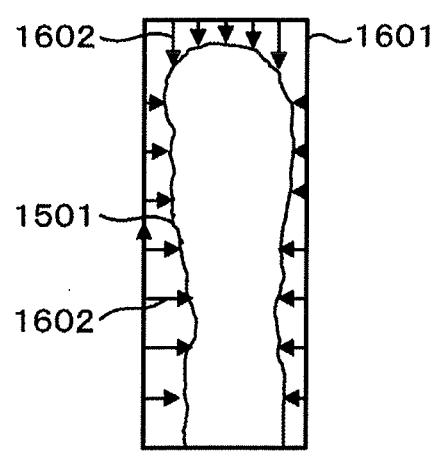
FIG. 16 is a diagram describing an example of measurement between layout data and contour lines.

According to setting on a GUI screen as exemplified in FIG. 21, it is possible to selectively carry out setting of contouring regions for the regions to which semiconductor pattern designers pay attention and it becomes possible to implement not only making the contouring processings efficient but also making measurement and inspection efficient. Incidentally, the pattern information on the design data can be acquired by accessing the design database 303 and necessary information can be read out based on settings on the GUI screen. Moreover, on the GUI screen exemplified in FIG. 21, there is provided a "Measurement Positions" input window so that setting of measurement portions can be done. Also, to enable measurement between the layout data and the formed contour lines ("Design/Contour") and measurement between the contour lines ("Contour/Contour"), respective input windows are provided. For example, based on an input to the "Design/Contour" input window, measurement as exemplified in FIG. 16 in measurement portions 1602 between layout data 1601 and a contour line 1501 is carried out.

Figure 22:
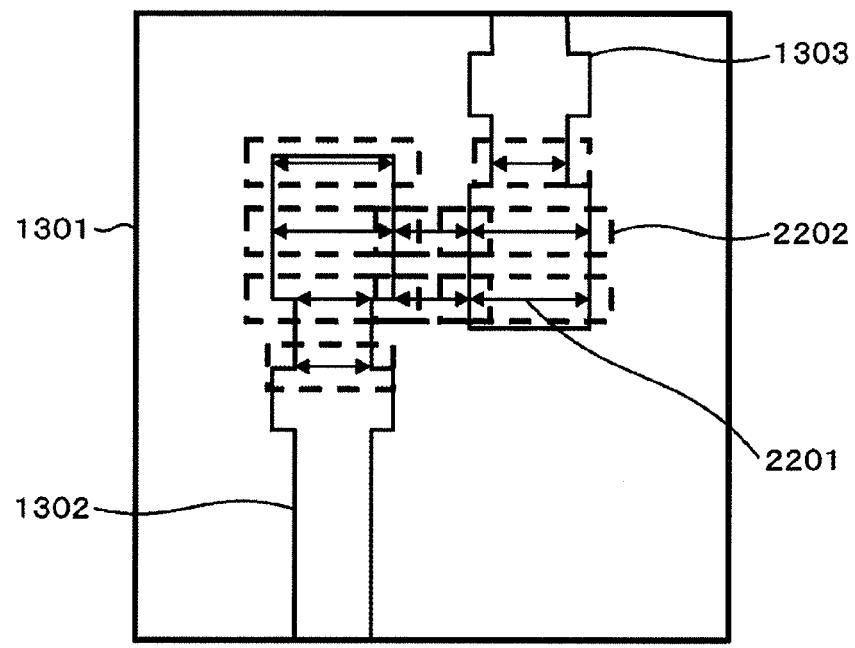
FIG. 22 is a diagram describing an example of setting contouring regions on the surroundings of a part of length measurement.
Figure 24:
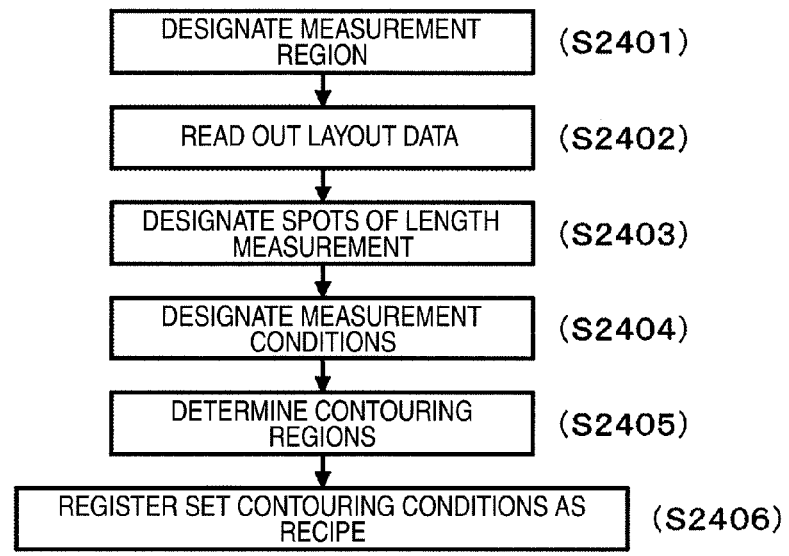
FIG. 24 is a flowchart describing processes of setting contouring regions on layout data.

3. Description of a Third Technique of Making Contouring Processing Steps More Efficient FIG. 22 is a diagram describing an example of a technique designed to make measurement and inspection efficient in the pattern region 1301 by carrying out contouring selectively regarding the portions of length measurement and not carrying out contouring processings regarding other portions. FIG. 24 is a flowchart describing the processing steps thereof. First, the measurement position (measurement region 1301) on the layout data is designated (Step 2401). Next, the layout data of the region 1301 are read out (Step 2402). Next, designation of the spots of length measurement is carried out (Step 2403). In the example of FIG. 22, an example of setting nine spots of measurement portions 2210 is described. Next, after measurement conditions at these portions of length measurement 2210 are set (Step 2405), contouring regions are determined (Step 2405).

Figure 23:
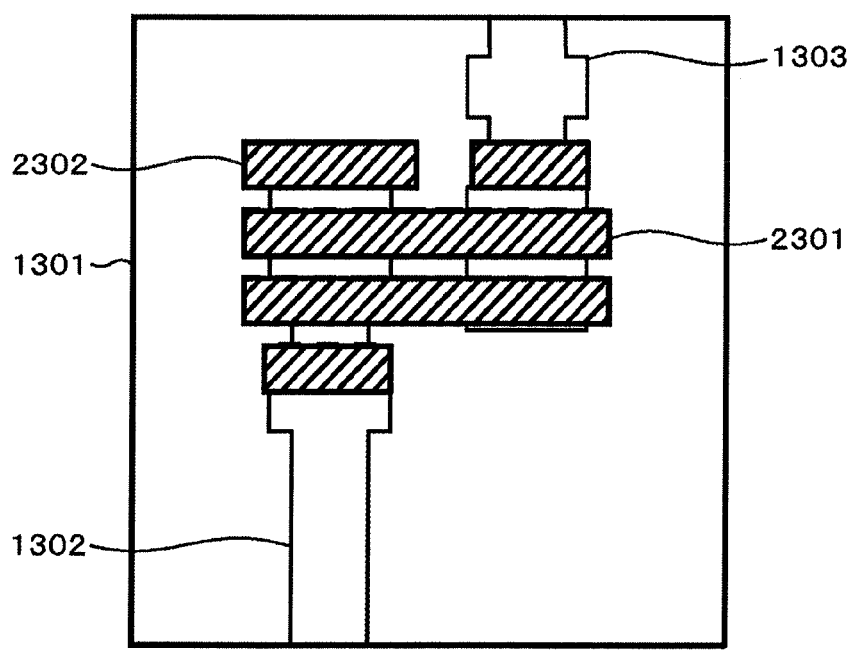
FIG. 23 is a diagram describing an example of setting contouring regions on the surroundings of a part of length measurement.

In Step 2405, it is also possible to set setting frames 2202 to define with which range contouring is executed with respect to the portion of length measurement. Based on such designation, contouring regions 2301 and 2302 are determined as exemplified in FIG. 23. By setting contouring regions automatically or semi-automatically based on setting of the portion of length measurement, it becomes possible to carry out contour line formation in agreement with intention of an operator while it is implemented to make contouring processings efficient.

The contouring conditions set as above are registered as a recipe controlling image processings during image acquisition (Step 2406). As mentioned above, since there is a possibility that influence of the optical proximity effect can be exercised on a wide range, the present technique, in which contouring regarding the surroundings of the portion of length measurement is readily set, is a particularly valid technique from the viewpoint of making setting of measurement conditions efficient as well. Also, according to the present technique of selectively contouring the surroundings of the portion of length measurement, matching of the measurement results and the contour lines of the neighborhood of the portion of length measurement also becomes easy so that it becomes possible to readily grasp the meanings held by the measurement results by comparison of the pattern profile and the measurement results. By storing contour lines partially extracted and measurement results with their associations and enabling display of information of both, comparison mentioned above becomes possible.

Figure 25:
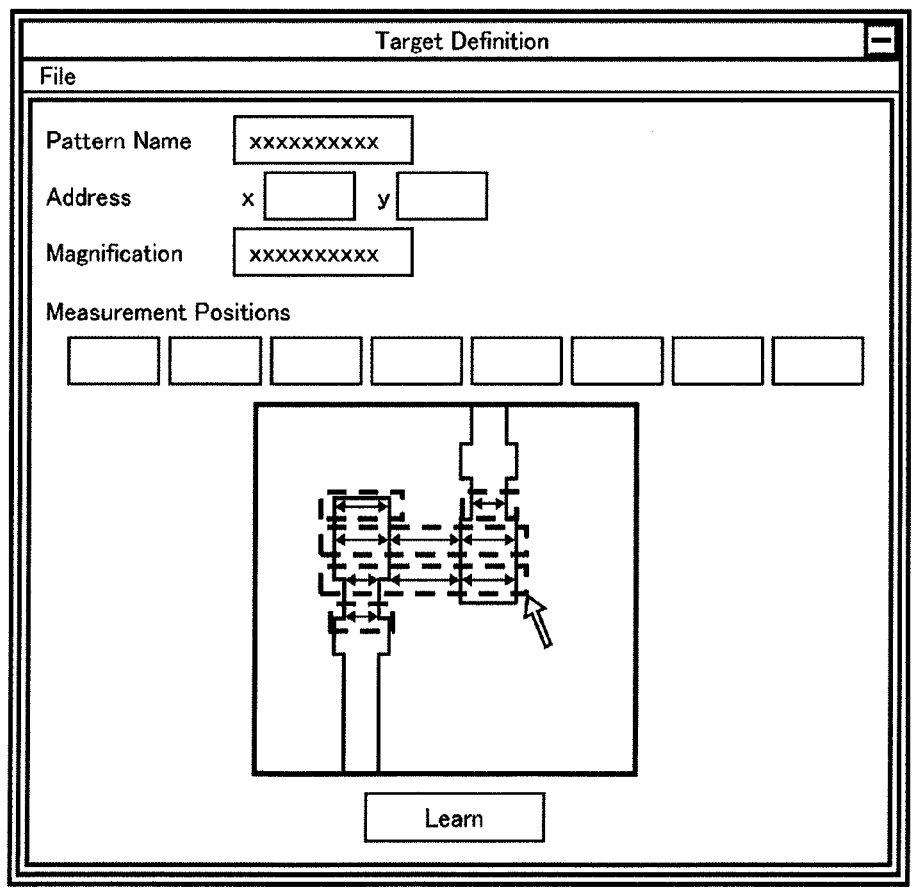
FIG. 25 is a diagram describing an example of a GUI screen for setting contouring regions.

FIG. 25 is a diagram describing an example of a GUI screen for setting portions of length measurement and contouring regions. An operator designates information related with the measurement region by designating a name of a pattern or a region in which a pattern is present ("Pattern Name"), coordinates where a pattern is present ("Address"), the size of an image that is actually acquired ("Magnification"), and the like on this screen. On this occasion, along with designation of "Measurement Positions", it is acceptable to designate the size of the contouring regions; it is also acceptable to automatically set the contouring regions so as to surround the portion of length measurement based on region information set in advance.

It should be further understood by those skilled in the art that although the foregoing description has been made on embodiments of the invention, the invention is not limited thereto and various changes and modifications may be made without departing from the spirit of the invention and the scope of the appended claims.

REFERENCE SIGNS LIST

301 Measurement recipe setting part
302 Measurement part
303 Design database
304 Layout database
305 OPC model database
306 OPC simulation database
307 OPC risk site database
308 Input device
309 Display device
1701 Data management device

The invention claimed is:

1. A contour line extraction method extracting contour lines of pattern edges on an image formed based on charged particles emitted from a sample due to irradiation of a charged particle beam, comprising:
  a step of performing contouring of a pattern located in an overlapping region provided in connecting images of a plurality of image-capturing regions to form a synthesized image, which further comprises:
    a step of finding either areas of said pattern in said plurality of image-capturing regions, or a portion of measurement set in advance; and
    a step of carrying out selective contour line extraction of said pattern with respect to an image of an image-capturing region either on a side where said area is large, or on a side where a portion of measurement regarding said pattern is located.

2. The contour line extraction method according to claim 1, wherein said overlapping region is a connecting region between a plurality of image-capturing regions.

3. The contour line extraction method according to claim 1, wherein information pertaining to an area of a pattern located in said overlapping region is read out from design data of said sample to find areas of said pattern in said plurality of image-capturing regions.

4. The contour line extraction method according to claim 3, wherein regarding said plurality of image-capturing regions, areas of said pattern are found to selectively perform contour line extraction of said pattern regarding an image of an image-capturing region for which said area is large and not to perform contour line extraction regarding rest of images of image-capturing regions.

5. A contour line extraction device comprising an arithmetic device extracting contour lines of a pattern displayed in an image from said image formed based on charged particles emitted from a sample due to irradiation of a charged particle beam; said arithmetic device finding either areas of said pattern in said plurality of image-capturing regions, or a portion of measurement set in advance, when contouring of a pattern located in an overlapping region provided in connecting images of a plurality of image-capturing regions to form a synthesized image is performed, so that selective contour line extraction of said pattern with respect to an image of an image-capturing region is carried out either on a side where said area is large, or on a side where a portion of measurement regarding said pattern is located.

6. The contour line extraction device according to claim 5, wherein said overlapping region is a connecting region between a plurality of image-capturing regions.

7. The contour line extraction device according to claim 5, wherein said arithmetic device reads out information pertaining to an area of a pattern located in said overlapping region from design data of said sample to find areas of said pattern in said plurality of image-capturing regions.

8. The contour line extraction device according to claim 7, wherein said arithmetic device finds areas of said pattern regarding said plurality of image-capturing regions to selectively perform contour line extraction of said pattern regarding an image of an image-capturing region for which said area is large and not to perform contour line extraction regarding rest of images of image-capturing regions.

9. A computer program product comprising a non-transitory computer readable medium having a computer readable program code embodied therein, the computer readable program code configured to perform operations comprising:
    accessing a storage medium storing design data of a semiconductor device or being provided with a storage medium storing said design data,
    extracting contour lines of a pattern displayed in an image from said image formed based on charged particles emitted from a sample due to irradiation of a charged particle beam, and
    when contouring of a pattern located in an overlapping region provided in connecting images of a plurality of image-capturing regions to form a synthesized image is performed,
        finding either areas of said pattern in said plurality of image-capturing regions, or a portion of measurement set in advance; and
        carrying out selective contour line extraction of said pattern with respect to an image of an image-capturing region either on a side where said area is large, or on a side where a portion of measurement regarding said pattern is located.

* * * * *